United States Patent [19]

Heck

[11] 3,960,932

[45] June 1, 1976

[54] PROCESS FOR THE PREPARATION OF ALDEHYDES FROM ORGANIC HALIDES

[75] Inventor: Richard F. Heck, Wilmington, Del.

[73] Assignee: The University of Delaware, Newark, Del.

[22] Filed: Oct. 10, 1974

[21] Appl. No.: 513,529

[52] U.S. Cl. .......................... 260/479 R; 260/289 R; 260/290 P; 260/326.16; 260/332.3 R; 260/465 R; 260/476 R; 260/562 R; 260/599; 260/600 R
[51] Int. Cl.² ......................................... C07C 45/00
[58] Field of Search ................ 260/479 R, 598, 599, 260/600, 601

[56] References Cited
OTHER PUBLICATIONS

Falbe, Carbon Monoxide in Org. Syn., (1970), pp. 118–120.

Maitlis, The Organic Chemistry of Palladium, Vol. II, (1971), p. 24.

Primary Examiner—James A. Patten

[57] ABSTRACT

Aldehydes are obtained from aryl, vinylic and heterocyclic halides and substituted derivatives thereof, a tertiary amine, carbon monoxide and hydrogen at from about 50°–175°C under from about one to 200 atmospheres pressure and with $PdX_2[P(C_6H_5)_3]_{1 \text{ or } 2}$ as a catalyst where X is acetate or a halogen. The ratios of carbon monoxide to hydrogen are not critical but the most favorable reactions are usually obtained with ratio from about 0.1 to about 10. A typical example is the conversion of p-bromoanisole to anisaldehyde in 84% yield at 150°C in 18 hrs. at 1000 psig. of 1:1 CO to $H_2$ with one mole percent of $PdBr_2[P(C_6H_5)_3]_2$ as catalyst and with tri-n-butylamine as the tertiary amine.

9 Claims, No Drawings

PROCESS FOR THE PREPARATION OF ALDEHYDES FROM ORGANIC HALIDES

This invention relates to a process for the preparation of aldehydes from organic halides by means of palladium catalysts, herein called formylation.

The Government has rights in this invention pursuant to Grant No. 73-75-GP-34492X awarded by the National Science Foundation.

Aldehydes are generally very useful compounds but are difficult to prepare. For example, benzaldehyde is prepared by the dichlorination of toluene and then in a second step the benzal chloride first produced is hydrolyzed to the aldehyde. In some cases alcohols are carefully oxidized to aldehydes but it is often difficult to stop at the aldehyde stage. In other cases more complex molecules are cleaved at a point of unsaturation to form aldehydes such as in the preparation of vanillin from isoeugenol. In still another method acid chlorides are reduced catalytically with hydrogen with specially deactivated catalysts to aldehydes.

It is the objective of this invention to produce aldehydes by a completely new and generally more economical method from organic halides having one carbon atom less than the aldehyde produced.

In accordance with this invention it has been found that aldehydes are obtained when aryl, vinylic, or heterocyclic bromides or iodides or certain chlorides such as 2-chloropropene are reacted at about 50°–200°C under at least one atmosphere of mixtures of carbon monoxide and hydrogen in the presence of a basic tertiary amine and a palladium catalyst. The process of this invention appears to depend upon the reactions broadly expressed as follows:

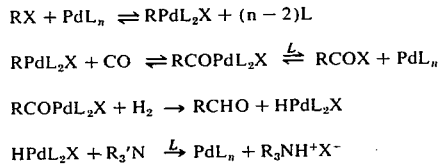

in which R is a aryl, vinylic or heterocyclic group or substituted derivative thereof, X is bromide or iodide or in some cases chloride, L is a coordinating group such as triphenylphosphine where $n$ is 2, 3 or 4 and $R_3'N$ is a basic tertiary amine in which the three R' groups may be the same or different.

It is evident from the reactions indicated above that this invention can be used to make aldehydes by contacting a carboxylic halide of the formula RCOX wherein R is an aryl, vinylic or heterocyclic group and X is a halide group particularly a chlorine or bromine, with either a mixture of carbon monoxide and hydrogen or pure hydrogen at about atmospheric pressure to about 200 atmospheres and at a temperature of about 50° to 200°C in the presence of a basic tertiary amine and a palladium catalyst of the formula $PdX_2(PR_3)_{1 \text{ or } 2}$ or $PdX_2(P(OR)_3)_{1 \text{ or } 2}$ or a reduced form thereof.

The above reactions of this invention may be carried out in an inert solvent such as benzene, xylene, toluene, excess tertiary amine or excess organic halide for example. A solvent is beneficial in some instances and improved yields may result from its use.

A wide variety of organic halides may be used in this invention. Generally an organic iodide is more reactive than the related chloride. In some cases the chlorides become so unreactive that they are not useful. For example 2-chloropropene reacts normally but p-chloroanisole is much less reactive under the same conditions. The reactivity, of course, depends upon the reaction conditions. Increasing temperatures increase the reaction rates but also increase the yield of by-products. Increasing the reaction pressure increases the yields of products but it may become uneconomical to use very high pressures.

Generally an equivalent or slight excess of the basic tertiary amine compared with the organic halide is used although this is not necessary. The reaction will stop, however, when the amine is used up so that the maximum yield of aldehyde under these conditions will be equal to the equivalents of amine used.

The preferred conditions for the reaction depend somewhat upon the organic halide that is being reacted since some react under much milder conditions than others. Generally, about a 5–20% excess of amine is combined with the organic halide with or without about an equal volume of a solvent such as benzene and about one mole percent of catalyst is added. This excess of amine is desirable as each mole of halide gives a mole of HX that has to be neutralized with basic amine for the reaction to continue. This mixture or solution is stirred under about 100 to 2000 psi of a 1:1 mixture of CO and hydrogen until no more gas is absorbed at a temperature of from about 75° to 175°C. The product can usually be isolated simply by washing the ether diluted reaction mixture with dilute aqueous acid to remove unreacted amine and amine salt and then distilling or subliming the product. The catalyst remains in the residue and often may be used over again without further treatment.

Examples of organic halides which may be used in this invention are: 2-chloro-2-butene, 1-chlorocyclohexene, 1-chlorocyclopentene, 4-chlorodiphenylsulphone, bromobenzene, iodobenzene, p-bromoanisole, 1-bromonaphthalene, 1-bromonaphthalene, dibromobenzene, chlorobromobenzene, methyl bromobenzoate, p-bromocyanobenzene, 4-acetoxy-3-methoxybromobenzene, 4-bromoveratrol, 4-bromocumene, p-bromobenzaldehyde, 2-iodotoluene, 2-bromobiphenyl, 2-chloropropene, 2-methyl-1-bromo-1-propene, 1-bromo-1-hexene, 3-iodo-3-hexene, trans-2-bromostyrene, α-bromostyrene, methyl 3-bromo-2-methylpropenoate, 1-bromocyclohexene, bromopyridine, bromothiophene, bromoquinoline and iodoindole.

The basic tertiary amine can be triethylamine, tri-n-propylamine, tri-isopropylamine, tri-n-butylamine, diisopropylethylamine and the like. Usually the trialkylamines are preferred over the less basic aryl amines and pyridine derivatives. Other basic materials that do not affect the catalyst and readily react with acids may be used in place of amines such as sodium carbonate, potassium acetate, lithium 2,6-di-t-butylphenoxide, lithium diisopropylamide etc. but amines have been found to be the most generally useful.

The catalyst for the reaction is a palladium complex or palladium metal which is converted into a soluble complex during the reaction. Organic iodides can be formylated with only simple palladium (II) salts such as the acetate or chloride or pyridine or benzonitrile complexes of these as catalysts or with finely divided metal, but bromides and chlorides usually require the presence of triorganic phosphorus compounds also with these materials in order to react. The most convenient triorganic phosphorus compound we have found is triphenylphosphine but many other related compounds may also be used such as tri-p-anisylphosphine, tri-p-tolyphosphine, tri-n-butylphosphine, triethylphosphine, triphenyl phosphite, trimethyl phosphite, trimethylolpropane phosphite, triphenylarsine and bisdiphenylphosphinoethane. These compounds are generally used in a ratio such that there will be two moles of phosphorus per mole of palladium although other ratios may also be used. Optimum results are usually found when the ratio of P:Pd is from about 0.5:1.0 to 5.0:1 with 2:1 being the preferred ratio mainly because this is the ratio that occurs in most stable complexes and these are convenient to employ as catalysts. Complexes such as $PdBr_2[P(C_6H_5)_3]_2$, $PdCl_2[P(C_6H_5)_3]_2$, for example, were often used. The amount of catalyst used in the formylation can be varied widely but of course the rate of the reaction depends upon how much is present. Convenient reaction rates were generally found when about one or two mole percent catalyst in the form of $PdX_2[P(C_6H_5)_2]_2$ was used. Insoluble forms of the catalyst may also be used if polymeric or inorganic supports which bind the palladium salts are used. In such cases only one organic phosphorous group may be attached to each palladium. Formylation may also be done in the vapor phase with only the catalyst not in the gas phase.

The relative amounts of carbon monoxide and hydrogen supplied to the formylation reactions is usually not critical. A 1:1 mixture is most convenient to obtain and use since the two gases are used up in that ratio but ratios of from about 0.1:1.0 to 1.0:0.1 could also be employed.

The reaction temperature is preferably kept as low as possible so that the aldehyde products do not undergo decomposition or further reactions under the reaction conditions. The temperature necessary to obtain practical reaction rates is dependent upon the organic halide used and the other conditions but usually temperatures from about 75°–175°C are preferred. The reactions proceed best if the liquid (if it is carried out in the liquid phase) and gas phases are thoroughly mixed together during the reaction.

It is clear from the equations presented above which are believed to be the basis of this invention that carboxylic acid halides should be reduced under the conditions of the reactions, to aldehydes since they are or at least may be under some conditions, intermediates in the reactions. This is indeed the case. Since acid chlorides are generally much more reactive than aryl, vinylic or heterocyclic chlorides, the acid chloride derivatives may be used under conditions where the related aryl, vinylic or heterocyclic chloride might react only very slowly. The reduction of the acid halide also does not require the presence of carbon monoxide and aldehydes may be obtained from acid halides by reaction with only hydrogen and the palladium catalyst.

The following examples illustrate various ramifications of this invention but the invention is not to be limited thereby.

EXAMPLE 1

Into a 45 ml stainless steel pressure reactor was placed 0.2 mmole $PdBr_2[P(C_6H_5)_3]_2$, 6.88 mmoles bromobenzene, 7.6 mmoles tri-n-butylamine and 1.5 ml of p-xylene. The reactor was sealed and flushed with carbon monoxide and then pressured to 1320 psig with a 1:1 mixture of carbon monoxide and hydrogen and stirred magnetically in an oil bath for 24 hrs. at 125°C. After cooling and venting, analysis of the reaction mixture by gas chromatography showed that benzaldehyde had been produced in 94% yield.

EXAMPLE 2

A reaction was carried out as in Example 1 but with iodobenzene instead of bromobenzene and with $PdI_2[P(C_6H_5)_3]_2$ instead of $PdBr_2[P(C_6H_5)_3]_2$. After 9 hrs. reaction at 125°C there was obtained a 95% yield of benzaldehyde.

EXAMPLE 3

The procedure of Example 1 was used with $PdBr_2[(4-CH_3C_6H_4)_3P]_2$ instead of $PdBr_2[(C_6H_5)_3P]_2$. Benzaldehyde was produced in high yield.

EXAMPLE 4

The procedure of Example 1 was used with $PdBr_2[(C_6H_5O)_3P]_2$ instead of $PdBr_2[(C_6H_5)_3P]_2$. Benzaldehyde was the product formed.

EXAMPLE 5

A mixture of 0.25 mmole $PdBr_2[P(C_6H_5)_3]_2$, 19 mmoles tri-n-butylamine and 17.2 mmoles p-bromoanisole was placed in a 45 ml pressure vessel and pressured to 1450 psig with a 1:2 mixture of carbon monoxide and hydrogen. The reaction mixture was heated to 150°C for 10 hrs. with magnetic stirring during which time the gas pressure dropped to 1100 psig. After cooling and venting the reaction mixture was diluted with ether, washed with dilute aqueous hydrochloric acid, dried over anhydrous magnesium sulfate and distilled under reduced pressure. There was obtained 1.97 g of p-methoxybenzaldehyde, b.p. 73°–75°C at 0.7 mm which is 84% of the theoretical amount.

EXAMPLE 6

A mixture of 0.25 mmole $PdBr_2[P(C_6H_5)_3]_2$, 19 mmoles tri-n-butylamine and 17.2 mmoles 1-bromonaphthalene was formylated under 1225 psig of a 1:1 mixture of carbon monoxide and hydrogen at 125°C for 24 hrs. with magnetic stirring. There was isolated from the reaction mixture an 82% yield of 1-naphthaldehyde, b.p. 147°–149°C (12mm) and 17% naphthalene.

EXAMPLE 7

A reaction was carried out as in Example 6 with p-bromobenzonitrile used in place of 1-bromonaphthalene and p-cyanobenzaldehyde was obtained as a product.

EXAMPLE 8

A reaction was carried out in Example 6 with methyl p-bromobenzoate instead of 1-bromonaphthalene and p-carbomethoxybenzaldehyde was obtained as a product.

EXAMPLE 9

A reaction was carried out in Example 6 except that 4-bromoveratrole was used in place of 1-bromonaphthalene. There was obtained as a product 3,4-dimethoxybenzaldehyde in 74% yield.

EXAMPLE 10

A mixture of 25 mmoles 4-acetoxy-3-methoxybromobenzene, 30 mmoles of tri-n-butylamine, 5 ml benzene, and 0.375 mmole PdBr$_2$[P(C$_6$H$_5$)$_3$]$_2$ was stirred under 1520 psig of a 1:1 mixture of carbon monoxide and hydrogen at 145°C for 26 hrs. From the reaction mixture there was isolated vanillin acetate, b.p. 123°–127°C (1 mm), in 78% yield. The m.p. after recrystallization from methanol was 74°–76°C.

EXAMPLE 11

A combination of 25 mmoles 1,4-dibromobenzene, 60 mmoles tri-n-butylamine, 15 ml benzene and 0.10 mmole PdBr$_2$[P(C$_6$H$_5$)$_3$]$_2$ was formylated under 1340 psig initial pressure of 1:1 carbon monoxide and hydrogen at 145°C for 24 hrs. The reaction mixture contained an 83% yield of terephthaldehyde, m.p. 112°–114°C and 23% of recoverable 1,4-dibromobenzene which were separated by chromatography on silica gel.

EXAMPLE 12

In a 75 ml stainless steel reaction vessel was placed 25 mmoles of trans-2-bromostyrene, 30 mmoles tri-n-butylamine, 5 ml benzene and 0.375 mmole PdBr$_2$[P(C$_6$H$_5$)$_3$]$_2$. The vessel was sealed under 1430 psig of a 1:1 mixture of carbon monoxide and hydrogen and heated with magnetic stirring at 100°C for 10 hours. Analyses of the reaction mixture showed that cinnamaldehyde had been formed in the reaction.

EXAMPLE 13

A mixture of 25 mmoles 3-bromopyridine, 10 ml triethylamine, 10 ml benzene and 0.375 mmole PdBr$_2$[(P(C$_6$H$_5$)$_3$]$_2$ was reacted under 1350 psig of 1:1 carbon monoxide and hydrogen at 145°C for 26 hrs. There was formed 3-pyridinealdehyde, b.p. 79°–81°C (12 mm) in 80% yield.

EXAMPLE 14

A mixture of 17 mmoles 2-bromothiophene, 19 mmoles tri-n-butylamine and 0.25 mmole PdBr$_2$[P(C$_6$H$_5$)$_3$]$_2$ was heated at 130°C with magnetic stirring under 1250 psig of 1:1 carbon monoxide and hydrogen for 20 hrs. There was isolated from the reaction mixture a 76% yield of 2-thiophenealdehyde, b.p. 78°–79°C (12 mm).

EXAMPLE 15

A reaction was carried out as in Example 12 except with 2-iodoquinoline instead of trans-2-bromostyrene. The product was 2-quinolinealdehyde.

EXAMPLE 16

An example similar to Example 11 was carried out with 1,2-dibromobenzene rather than the 1,4-isomer and benzaldehyde was obtained.

EXAMPLE 17

A reaction was carried out as in Example 11 but with 1,3-dibromobenzene rather than 1,4-dibromobenzene and the product was isophthaldehyde.

EXAMPLE 18

A reaction was carried out as in Example 12 except that 3-iodo-3-hexene was used in place of 2-bromostyrene and PdI$_2$[P(C$_6$H$_5$)$_3$]$_2$ was used instead of PdBr$_2$[P(C$_6$H$_5$)$_3$]$_2$. The product was 2-ethyl-2-pentenal.

EXAMPLE 19

A reaction was carried out as in Example 12 with 1-bromo-1-hexene in place of 2-bromostyrene and the product was 2-heptenal.

EXAMPLE 20

A reaction was carried out as in Example 5 with 4-bromoacetanilide in place of p-bromoanisole and 4-acetamidobenzaldehyde was formed.

EXAMPLE 21

A mixture of 25 mmoles of benzoyl chloride, 30 mmoles tri-n-butylamine, 10 ml benzene, and 0.375 mmole PdCl$_2$[P(C$_6$H$_5$)$_3$]$_2$ was reacted at 125°C with a 1:1 mixture of carbon monoxide and hydrogen at 1380 psig for 12 hrs. and benzaldehyde was formed in 83% yield.

EXAMPLE 22

A reaction similar to Example 21 was carried out with 600 psig of (only) hydrogen and benzaldehyde was formed in 81% yield.

EXAMPLE 23

A reaction similar to Example 21 was carried out with o-anisoyl chloride instead of benzoyl chloride and o-anisoldehyde was produced.

The variation shown in Examples 21, 22 and 23 illustrates a simple reduction of an acid halide to an aldehyde. Since acid halides may be intermediates in these reactions it is possible to start with the intermediate also. This variation is useful when the acid halide is more readily available than the organic halide with one less carbon atom.

The products of this invention are extremely useful organic compounds. Besides important uses as chemical intermediates aldehydes are used frequently in the perfume and flavoring industries. For example, benzaldehyde, cinnamaldehyde, p-methoxybenzaldehyde and vanillin are all used by these industries and these materials can be prepared by means of the invention. The process of this invention is superior to the previously known methods because it allows a halogen group to be replaced by a formyl group and this reaction was not possible heretofore.

As many apparently widely different embodiments of this invention may be made without departing from the spirit and scope thereof it is to be understood that this invention is not limited to the specific embodiments thereof except as defined in the appended claims.

I claim:

1. A process for the preparation of aldehydes which comprises contacting aryl, vinylic and heterocyclic halides with carbon monoxide and hydrogen at about 0.1 to 1.0 to about 1.0 to 0.1 ratios under pressures of at least one atmosphere at temperatures in the range of 50° to about 175°, in the presence of a palladium catalyst and a basic tertiary amine or other basic material inert to the catalytic function of the catalyst that will readily react with acids.

2. The process of claim 1 wherein the palladium catalyst is a complex of formula PdX$_2$(PR$_3$)$_{1 \text{ or } 2}$ or PdX$_2$(P(OR)$_3$)$_{1 \text{ or } 2}$ or a reduced form thereof where X is acetate, bromide, chloride or iodide and R is a alkyl, cycloalkyl, aryl, phenoxy, alkoxy or substituted amide group or a combination of reagents is used which produces one of these catalysts or a reduced form thereof under the reaction conditions.

3. The process of claim 2 wherein the aryl, vinylic and heterocyclic halides are bromide or iodides.

4. The process of claim 2 wherein the vinylic halides are chlorides.

5. A process for the production of aldehydes which comprises contacting a carboxylic acid halide of the formula RCOX wherein R is an aryl, vinylic or heterocyclic group and X is a halide group with a mixture of carbon monoxide and hydrogen or pure hydrogen in the presence of a basic tertiary amine at about atmospheric pressure to about 200 atmospheres and at about 50° to about 175° in the presence of a palladium catalyst of formula $PdX_2(PR_3)_{1\ or\ 2}$ or $PdX_2(P(OR)_3)_{1\ or\ 2}$ or a reduced form thereof.

6. The process of claim 2 wherein the reactant is bromobenzene and the product is benzaldehyde.

7. The process of claim 2 wherein the reactant is p-bromoanisole and the product is p-methoxybenzaldehyde.

8. The process of claim 2 wherein the reactant is 1,4-dibromobenzene and the product is terephthaldehyde.

9. The process of claim 2 wherein the reactant is 4-acetoxy-3-methoxybromobenzene and the product is vanillin acetate.

* * * * *